United States Patent
Krys

(10) Patent No.: US 6,321,560 B1
(45) Date of Patent: Nov. 27, 2001

(54) APPARATUS AND METHOD FOR COOLING

(76) Inventor: William George Krys, 12112-50 Street, Edmonton, Alberta (CA), T5W 3C5

( * ) Notice: Subject to any disclaimer, the term of this patent is extended or adjusted under 35 U.S.C. 154(b) by 0 days.

(21) Appl. No.: 09/558,653

(22) Filed: Apr. 26, 2000

Related U.S. Application Data

(60) Provisional application No. 60/131,490, filed on Apr. 29, 1999.

(51) Int. Cl.⁷ ................................. F25D 9/00; F28B 9/00
(52) U.S. Cl. ................................. 62/402; 62/172
(58) Field of Search ............................ 62/401, 402, 87, 62/88, 172

(56) References Cited

U.S. PATENT DOCUMENTS

| | | | | |
|---|---|---|---|---|
| 888,206 | * | 5/1908 | Tuerk | 62/401 |
| 1,938,205 | * | 12/1933 | Yeomans | 62/402 |
| 2,585,570 | * | 2/1952 | Messinger et al. | 62/402 |
| 2,664,001 | * | 12/1953 | Brisken et al. | 62/402 |
| 2,928,261 | * | 3/1960 | Sampietro | 62/402 |
| 4,058,384 | * | 11/1977 | Keefe | 62/457.9 |
| 5,438,845 | * | 8/1995 | Kirschner et al. | 62/172 |
| 5,718,116 | * | 2/1998 | Grassi et al. | 62/62 |
| 5,823,008 | * | 10/1998 | Nikai et al. | 62/401 |

* cited by examiner

*Primary Examiner*—William Doerrler
(74) *Attorney, Agent, or Firm*—Ridout & Maybee LLP

(57) ABSTRACT

An apparatus for cooling a target in a region having a first pressure. The apparatus includes a compressor for compressing a gas to a second pressure higher than the first pressure, means for cooling the compressed gas to a selected temperature downstream of the compressor, and means for discharging the compressed gas towards the target at a selected rate downstream of the cooling means. A pressure tank is provided downstream of the compressor for receiving compressed gas from the compressor and supplying the gas to the discharging means. The second pressure, selected temperature, and selected rate are chosen so as to cool the target upon expansion of the gas in the region. A method of cooling a target using the apparatus is also disclosed.

18 Claims, 3 Drawing Sheets

APPARATUS AND METHOD FOR COOLING

The present application claims the benefit under 35 U.S.C. Section 119(e) of U.S. provisional application Ser. No. 60/131,490 filed Apr. 29, 1999.

FIELD OF THE INVENTION

The present invention relates to an apparatus and method for cooling bodies or chambers using the phenomenon of cooling by decompression and expansion of compressed gas.

BACKGROUND TO THE INVENTION

Methods for cooling bodies, such as objects, in gases is known. For example, objects are cooled in commonly-used refrigerators and freezers by contact with cooled air. The air is cooled by passing relatively warm air over a heat exchanger in which there is a cooler fluid. The fluid is cooled by evaporative cooling of a low boiling liquid, e.g. a CFC or HCFC fluorocarbon, in a closed cycle system.

Methods for cooling gases and liquids are also known, apart from evaporative cooling. One method involves bubbling gas though a cool liquid. For example, M. A. Krongold, in U.S. Pat. No. 4,607,489, which issued Aug. 26, 1986, discloses cooling gas by bubbling the gas through a cryogenic liquid. B. Adolfsson, in PCT Publication WO95/09124, published Apr. 6, 1995, discloses introducing carbon dioxide below the surface of a liquid, wherein the expansion of the carbon dioxide cools the liquid.

The phenomenon of cooling gases by their expansion is known. The present invention utilizes this phenomenon to cool a target such as bodies or chambers, preferably without the necessity of closed cycle systems or environmentally or physiologically problematic materials such as CFCs or HCFCs.

SUMMARY OF THE INVENTION

Accordingly, the invention provides an apparatus for cooling a target in a region having a first pressure. The apparatus includes a compressor for compressing a gas to a second pressure higher than the first pressure, means for cooling the compressed gas to a selected temperature downstream of the compressor, means for discharging the compressed gas towards the target at a selected rate downstream of the cooling means, and a pressure tank downstream of the compressor for receiving compressed gas from the compressor and supplying the gas to the discharging means. The second pressure, selected temperature, and selected rate are chosen so as to cool the target upon expansion of the gas in the region.

In a first embodiment, the apparatus may be for cooling a chamber. The chamber may be a vehicle interior, such as a cabin of an automobile, a room in a building, or an interior of a movable structure, such as a trailer. The gas may be air and the discharging means may be adapted to discharge air into the chamber.

In a second embodiment, the apparatus may be for cooling a part of an animal and the discharging means may be in the form of a hand-manipulable tube with an expansion nozzle at one end of the tube.

In a third embodiment, the apparatus may be for cooling a liquid. The discharging means may be positioned in the liquid for discharging compressed gas into the liquid to thereby cool the liquid.

There may be two or more of the aforesaid pressure tanks arranged in parallel for alternately receiving compressed air from the compressor and alternately supplying the air to the discharging means.

The cooling means may be associated with the pressure tank to cool compressed gas in the pressure tank to the selected temperature.

Furthermore, the compressor may be a primary compressor and the pressure tank may be a primary pressure tank. The apparatus may further include an ancillary compressor upstream of the primary compressor for pre-compressing air to be further compressed by the primary compressor, and an ancillary pressure tank, downstream of the ancillary compressor, for receiving compressed air from the ancillary compressor and supplying compressed air to the primary compressor.

The apparatus may further include a turbine downstream of the primary pressure tank and coupled to the ancillary compressor, the turbine being adapted to receive compressed air from the primary pressure tank and convert energy in the compressed air into energy for powering the ancillary compressor.

The apparatus may also include means associated with the primary compressor for selectively taking air from the ancillary pressure tank or the is atmosphere and directing the air to the primary compressor.

The primary compressor may be adapted to compress air to between 290 psi and 3000 psi.

The selected temperature may be about ambient temperature and the cooling means may be a heat exchanger. Furthermore, there may be a fan associated with the heat exchanger for cooling the heat exchanger.

In accordance with another aspect, the invention provides a method for cooling a target in a region having a first pressure including the steps of:

(a) providing a compressor for compressing a gas to a second pressure greater than the first pressure;

(b) providing means for cooling the compressed gas to a selected temperature downstream of the compressor;

(c) providing means for discharging the gas towards the target in the region at a selected rate; and (d) providing a pressure tank, downstream of the compressor and upstream of the discharging means, for receiving compressed gas from the compressor and supplying the gas to the discharging means;

wherein the second pressure, selected temperature, and selected rate are chosen so as to cool the target upon expansion of the gas in the region.

BRIEF DESCRIPTION OF THE DRAWINGS

Preferred embodiments of the invention will now be described with reference to the drawings in which.

DETAILED DESCRIPTION OF THE PREFERRED EMBODIMENTS

Figure 1:
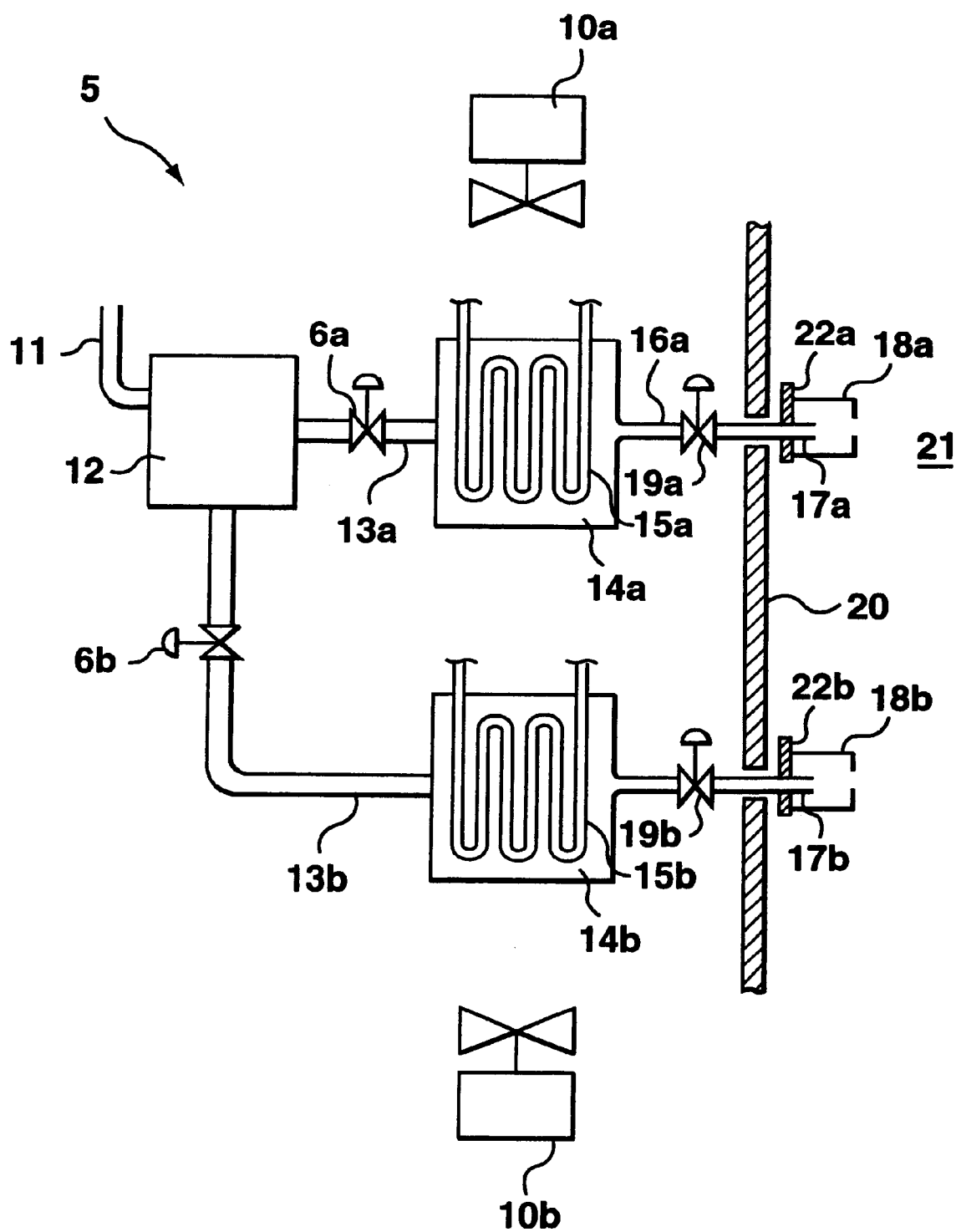
FIG. 1 is a diagrammatic view of an apparatus according to a first preferred embodiment of the invention in the form of an air conditioner for a cabin of an automobile.

Referring to FIG. 1, an air conditioner 5 for a vehicle (which in this embodiment is an automobile) according to a first preferred embodiment, is shown. The air conditioner 5 has an air inlet 11 which leads into a compressor 12 for compressing the air, as will be further described. Compressor 12 is connected to a pair of parallel pressure tanks 14a, 14b by means of respective pipes 13a, 13b. The pressure tanks 14a, 14b store compressed air received from the compressor 12 for subsequent discharge. Furthermore, the pressure tanks 14a, 14b have respective heat exchangers 15a, 15b therein for cooling the stored compressed air to about ambient temperature. The heat exchangers 15a, 15b are in turn cooled by respective fans 10a, 10b in a known manner. Pressure tanks 14a, 14b are connected to respective tubes 16a, 16b leading into a cabin 21 of the automobile. The tubes 16a, 16b have respective outlets 17a, 17b which, in turn, have respective mufflers 18a, 18b and filters 22a, 22b associated therewith for reasons as will be explained. Control valves 19a, 19b are provided in the tubes 16a, 16b for controlling the discharge of cooled compressed air, as will also be further explained.

In operation, air from outside the automobile is sucked into compressor 12 and compressed to a selected pressure higher than the pressure in the cabin 21 (which, in this example, is about 14.65 psi or about 101 Kpa). In this embodiment, the selected pressure is approximately 1600 psi. However, the pressure may be in the range of about 290 psi to about 2900 psi (about 2 Mpa to about 20 Mpa). Control means (not shown) regulates valves 6a, 6b to cause compressed air from compressor 12 to be supplied alternately to pressure tanks 14a, 14b when pressure within the pressure tanks 14a, 14b falls below a threshold value. Similarly, the control means turns compressor 12 off when the pressure within pressure tanks 14a, 14b is at or above the threshold value. The pressure tanks 14a, 14b store the compressed air which is cooled by the heat exchangers 15a, 15b to about ambient temperature as determined by temperature sensors (not shown) in the pressure tanks 14a, 14b.

When the cabin 21 is to be cooled, as determined by a thermostat (not shown) contained in the cabin 21, the control means opens one of the valves 19a, 19b and cooled compressed air is discharged into the cabin 21 from the associated pressure tank 14a, 14b through the associated tube 16a, 16b, and outlet 17a, 17b. The expansion of the cooled compressed air into the cabin 21 produces a cooling effect. If the supply of cooled compressed air contained in the subject pressure tank 14a, 14b has been reduced to a level insufficient to effect cooling of the cabin 21, the valve 19a, 19b that was opened is closed and the other valve 19a, 19b is opened to allow cooled compressed air to be discharged from the other pressure tank 14a, 14b. As mentioned above, the supply of compressed air within pressure tanks 14a, 14b is replenished automatically by the control means. However, the compressed air is not discharged from the pressure tanks 14a, 14b until it has been cooled to about ambient temperature. It will be appreciated that the capacity of the compressor 12 to compress air, and the capacity of the heat exchangers 15a, 15b to cool the compressed air in the pressure tanks 14a, 14b, will be engineered (as is known in the art) to ensure that there is a constant supply of cooled compressed air available to cool the cabin 21 when required.

In this embodiment, the cooled air produced by expansion of the compressed air is circulated within the cabin by means of a fan (not shown). However, circulation of cooled air may also occur merely by convection and the kinetic energy of the released air.

The mufflers 18a, 18b are provided to reduce the noise from expansion of the air. The filters 22a, 22b are used to clean the discharged air of dust and other airborne particles.

The compressor 12 is powered by the motor of the automobile. The cooling heat exchangers 15a, 15b associated with the pressure tanks 14a, 14b are placed so that air may pass over the heat exchangers 15a, 15b in the same way as air passes over the radiator for the motor of the automobile. Thus, the cooling effect of the fans 10a, 10b, is supplemented by the cooling produced by outside air flowing over the heat exchangers 15a, 15b while the automobile is in motion. When the automobile is stationary, the fans 10a, 10b provide the only source for cooling of the heat exchangers 15a, 15b.

It will be understood that, for greater energy and cooling efficiency, some of the air from the cabin 21 can be recirculated into intake 11. It will be further understood that in order to minimize ice build-up within the air conditioner 5, means can be provided to remove moisture from the compressed air, in a known manner.

The heat exchangers 15a, 15b, although being internal to pressure tanks 14a, 14b, may alternatively be external to pressure tanks 14a, 14b, e.g. cooling fins on the outside of the tanks. In this embodiment, the heat exchangers are cooled using fans 10a, 10b. However, it will be appreciated that the heat exchangers may be a part of known closed cycle cooling systems is employing a low boiling fluid therein, e.g. a CFC or HCFC. In the alternative, the heat exchangers may be cooled using known water cooling systems.

It will appreciated that there may be more than two pressure tanks in parallel or there may be only a single pressure tank, as in the case of the other preferred embodiments of the invention to be now described. In such cases, the capacity of the compressor and cooling means will be adjusted accordingly.

Figure 2:
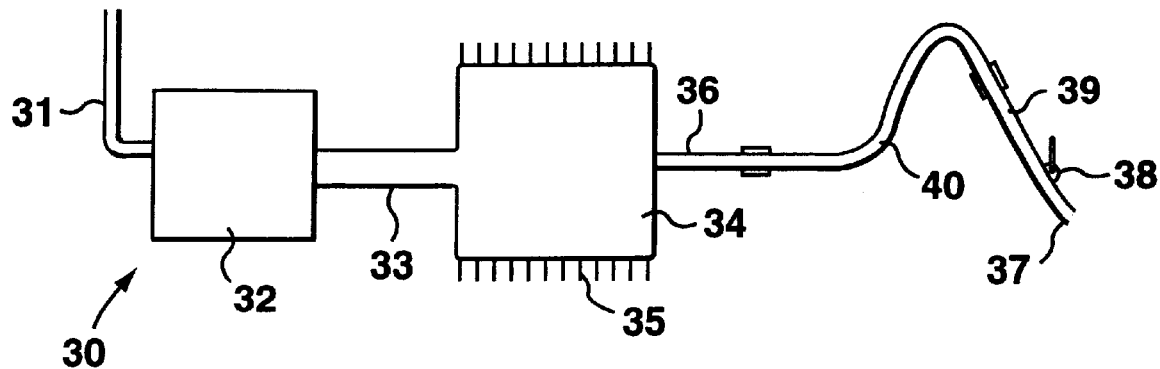
FIG. 2 is a diagrammatic view of an apparatus according to a second preferred embodiment of the invention in the form of a hand tool for cooling parts of animals.

Referring to FIG. 2, a hand tool 30 for cooling parts of animals or humans, such as warts, is shown. The hand tool 30 has an air inlet 31, compressor 32, air outlet 33, and pressure tank 34 with external cooling fins 35 for cooling the air in the pressure tank 34 to close to ambient temperature. A flexible tube 36 from pressure tank 34 is coupled to another flexible tube 40 which, in turn, is coupled to a tubular wand 39 having an expansion nozzle at one end. The expansion nozzle has a manually operable valve 38 close to an outlet 37 of the nozzle.

In operation, air from inlet 31 is compressed by compressor 32 and cooled in pressure tank 34. The compressed air is released on demand by means of the manually operable valve 38. Flexible tube 40 allows the outlet 37 to be directed to the part of the body to be cooled, e.g. a wart. Depending on the application, other gases may be used such as nitrogen, helium and carbon dioxide.

Figure 3:
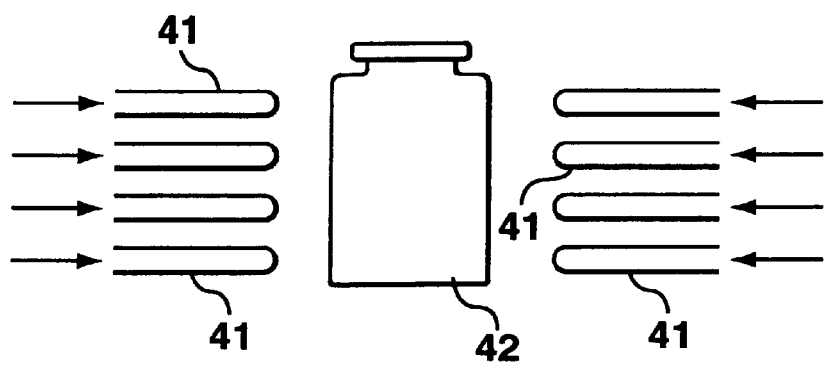
FIG. 3 is a schematic view of a container being cooled using a plurality of air jets.

FIG. 3 illustrates schematically another application of the principle employed by the present invention. Compressed gas is supplied to a plurality of jets 41 directed at a container 42. The expansion of compressed gas exiting the jets 41 cools the gas which, in turn, cools the container 42. The advantage of using a plurality of jets 41 is that cool gas may be applied to a large surface area of the container 42 thereby achieving an increase in the rate of cooling of the contents of the container 42. The rate of cooling is further increased by the fact that the gas is not essentially stationary as in the case of conventional refrigerators, for example.

Figure 4:
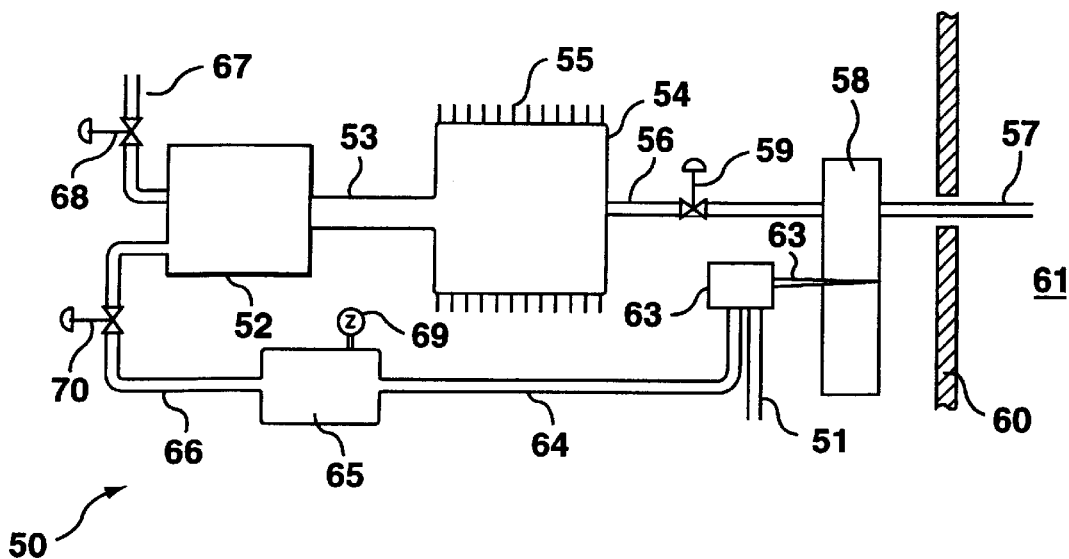
FIG. 4 is a diagrammatic view of an air conditioner for an automobile according to a third preferred embodiment of the invention.

Referring now to FIG. 4, an air conditioner 50 for cooling a cabin 61 of an automobile according to a third preferred embodiment of the invention is shown. The air conditioner 50 has an air inlet 51 which allows air to flow passively into an ancillary compressor 63 for compressing the air. In this embodiment, air inlet 51 is outside of the automobile cabin 61. However, inlet 51 may alternatively be inside cabin 61, or with suitable valves and controllers, there may be air inlets both inside and outside cabin 61. Ancillary compressor 63 is connected by pipe 64 to ancillary pressure tank 65 for storing compressed air from the ancillary compressor 63. Ancillary pressure tank 65 is, in turn, connected by pipe 66, via valve 70, to primary compressor 52 for further compressing the air. Primary compressor 52 also has an air inlet pipe 67 connected to an air inlet (not shown) outside cabin 61 from receiving air from atmosphere. It should be appreciated, however, that the air inlet may be inside cabin 61 or, with suitable valves and controllers, there may be air inlets both inside and outside cabin 61. Control means (not shown) operate to open a valve 68 in the air inlet pipe 67 when pressure in ancillary tank 65 is low, as detected by pressure gauge 69. When the pressure in ancillary tank 65 is at or above a threshold value, the control means causes valve 68 to close and valve 70 to open (as will be further described).

Primary compressor 52 is connected to a primary pressure tank 54 by means of a pipe 53. Primary pressure tank 54 stores compressed air from the primary compressor and has heat exchanger fins 55 attached thereto for cooling the compressed air stored in the tank 54 to about ambient temperature.

Primary pressure tank 54 is connected to tube 56 which has an outlet into turbine 58. Air entering turbine 58 is able to turn rotors (not shown) which are mounted on shaft 62. A tube 57 receives air leaving the turbine 58 and discharges it into the cabin 61. Tube 56 has a control valve 59 therein for regulating the discharge of cooled compressed air into the cabin 61. Turbine 58 is connected by shaft 62 to ancillary compressor 63. Thus, the flow of compressed air past the rotors of the turbine cause it to turn and generate current for powering ancillary compressor 63. In this embodiment, the compressors 52 and 63, and pressure tanks 54 an 65 are outside the cabin 61 and tube 57 extends through interior wall 60 into the cabin 61. Although, turbine 58 is outside cabin 61, it may alternatively be inside cabin 61.

In operation, when the cabin 61 needs to be cooled, as determined by a temperature sensor (not shown) in the cabin 61, valve 59 is opened by the control means and cooled compressed air is discharged through tube 56 from primary pressure tank 54. The compressed air partially expands and cools as it flows through turbine 58. Some of the kinetic energy of the expanding air is converted by the turbine 58 into useful power which is used to operate ancillary compressor 63 which compresses air from inlet 51. The compressed air is then stored in ancillary pressure tank 65.

When the pressure in ancillary pressure tank 65 is at or above a predetermined pressure, as determined by pressure gauge 69 of the control means, valve 68 is closed and valve 70 is opened so that the compressed air from the ancillary pressure tank can flow into primary compressor 52 for further compressing. The further compressed air is then stored and cooled to about ambient temperature in primary pressure tank 54. When the pressure in ancillary pressure tank 65 is below the predetermined pressure, valve 68 is opened and valve 70 is closed by the control means so that atmospheric air is drawn directly into primary compressor 52. Thus, this embodiment is intended to achieve some cost savings by capturing some of the energy from discharged air and using the energy to pre-compress air in the ancillary compressor.

As mentioned above, the air inlet connected to air inlet pipe 67 may be inside cabin 61. In such event, the apparatus 50 permits the recirculation of air within the system.

Figure 5:
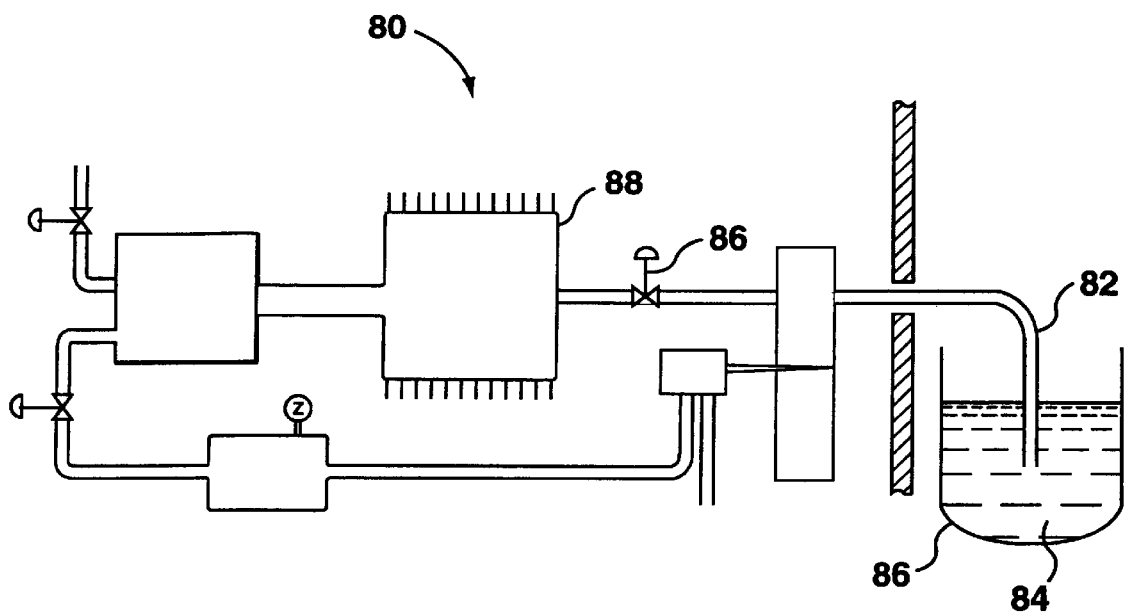
FIG. 5 is a diagrammatic view of an apparatus according to a fourth preferred embodiment of the invention for cooling liquids.

The air conditioner 50 may be modified for use in cooling liquids, as shown in FIG. 5 (which appears next to FIG. 2). This Figure shows a liquid cooling apparatus 80 which is similar in every respect to the air conditioner 50 except as follows. The apparatus 80 has an outlet 82 configured so that it may be positioned in a liquid 84 contained in a vessel 86. Thus, compressed air may be bubbled through the liquid 84 to cool the liquid 84. In this embodiment, the control means includes a manually operable switch (not shown) used to open valve 86 to release cooled compressed gas from a primary pressure tank 88. Thus, the discharge of the cooled compressed gas into the liquid may be controlled at will. It will be understood that other gases may be used such as carbon dioxide, and that the capacity of the compressors and cooling fins will vary to suit the application.

Although not shown in the drawings, the apparatus of the invention may be installed in a building for cooling a room of the building. In buildings with forced air heating, cooling and ventilating systems, cooled compressed air may be discharged into a plenum which leads into a forced air heating, cooling and ventilating system of the building.

The apparatus may also be installed in a trailer pulled by a truck or a refrigerator car pulled by a locomotive to cool the interiors of these structures.

As is known, the temperature differential between the compressed gas and expanded gas is controlled by the pressure differential. Therefore, the rate of cooling can be altered by altering the pressure to which the gas is compressed for a given pressure in the region of the target (i.e. object or chamber) to be cooled. The rate of cooling can also be altered by the rate of discharge of the compressed gas towards the target, as well as by the temperature to which the pressurized gas is cooled by the cooling means of the apparatus prior to discharge. It will be appreciated that the pressure to which the gas is compressed, the temperature to which the gas is cooled, and the rate of discharge of the gas towards the target are selected to effect the desired cooling of the target, will vary to suit the particular application, and can be determined by simple experimentation.

One advantage of the present invention is the use of universally available gases, e.g. air, as the cooling medium, instead of CFCs, HCFCs, etc., for example. Another advantage associated with systems having electrically driven compressors is that the capacity for cooling can be generated at times when demand for electricity is off peak, thus providing for more efficient use of electrical generating resources.

It will be appreciated that the foregoing description is by way of example only and is not meant to limit the scope of the invention as defined by the following claims.

I claim:

1. An apparatus for cooling a target in a region having a first pressure comprising:

a compressor for compressing a gas to a second pressure higher than said first pressure;

means for cooling the compressed gas to a selected temperature downstream of said compressor;

means for discharging the compressed gas towards the target at a selected rate downstream of said cooling means; and a pressure tank downstream of said compressor for receiving compressed gas from said compressor and supplying said gas to said discharging means, said cooling means being associated with said pressure tank to cool compressed gas in said pressure tank to the selected temperature;

wherein said second pressure, selected temperature, and selected rate are chosen so as to cool said target upon expansion of the gas in said region.

2. An apparatus according to claim 1 wherein said gas is air and said discharging means is adapted to discharge air into a chamber.

3. An apparatus according to claim 1 wherein said selected temperature is about ambient temperature.

4. An apparatus according to claim 1 wherein said compressor is a primary compressor and said pressure tank is a primary pressure tank, said apparatus further comprising:

an ancillary compressor upstream of said primary compressor for precompressing gas to be further compressed by said primary compressor;

an ancillary pressure tank, downstream of said ancillary compressor, for receiving compressed gas from the ancillary compressor and supplying compressed gas to said primary compressor;

a turbine downstream of said primary pressure tank and coupled to said ancillary compressor, the turbine being adapted to receive compressed gas from said primary pressure tank and convert energy in the compressed gas into energy for powering said ancillary compressor; and means associated with said primary compressor for selectively taking gas from the ancillary pressure tank or the atmosphere and directing said gas to the primary compressor.

5. An apparatus according to claim 1 wherein said cooling means is a heat exchanger, said apparatus further comprising a fan associated with said heat exchanger for cooling said heat exchanger.

6. An apparatus according to claim 1 wherein said compressor is adapted to compress gas to between 290 psi and 3000 psi.

7. An apparatus according to claim 1 having a plurality of said pressure tanks arranged in parallel for alternately receiving compressed gas from the compressor and supplying said gas alternately to the discharging means.

8. An apparatus according to claim 3 having a plurality of said pressure tanks arranged in parallel for alternately receiving compressed gas from the compressor and supplying said gas alternately to the discharging means.

9. An apparatus for cooling a part of an animal in a region having a first pressure comprising:

a compressor for compressing a gas to a second pressure higher than said first pressure;

means for cooling the compressed gas to a selected temperature downstream of said compressor;

means for discharging the compressed gas towards the target at a selected rate downstream of said cooling means, said discharging means comprising a hand manipulable tube with an expansion nozzle at one end of the tube; and a pressure tank downstream of said compressor for receiving comprised gas from said compressor and supplying said gas to said discharging means;

wherein said second pressure, selected temperature, and selected rate are chosen so as to cool said target upon expansion of the gas in said region.

10. An apparatus according to claim 9 wherein said selected temperature is about ambient temperature.

11. An apparatus according to claim 1 for cooling a liquid wherein said discharging means may be positioned in a liquid for discharging the compressed gas in said liquid to cool said liquid.

12. An apparatus according to claim 11 wherein said selected temperature is about ambient temperature.

13. An apparatus according to claim 4 wherein said selected temperature is about ambient temperature.

14. An apparatus according to claim 4 for cooling a liquid wherein said discharging means may be positioned in a liquid for discharging the compressed gas in said liquid to cool said liquid.

15. An apparatus according to claim 4 wherein said primary compressor is adapted to compress gas to between 290 psi and 3000 psi.

16. An apparatus for cooling a target in a region having a first pressure comprising:

a compressor for compressing a gas to a pressure between about 290 psi and about 3000 psi;

means for cooling the compressed gas to about ambient temperature downstream of said compressor;

means for discharging the compressed gas towards the target at a selected rate downstream of said cooling means; and a pressure tank, downstream of said compressor and upstream of said discharging means, for receiving compressed gas from said compressor and supplying said gas to said discharging means, said cooling means being associated with said pressure tank to cool compressed gas in said pressure tank to about ambient temperature;

wherein said selected rate is chosen so as to cool said target upon expansion of the gas in said region.

17. An apparatus according to claim 16 wherein said compressor is a primary compressor and said pressure tank is a primary pressure tank, said apparatus further comprising:

an ancillary compressor upstream of said primary compressor for precompressing air to be further compressed by said primary compressor;

an ancillary pressure tank, downstream of said ancillary compressor, for receiving compressed air from the ancillary compressor and supplying compressed air to said primary compressor;

a turbine downstream of said primary pressure tank and coupled to said ancillary compressor, the turbine being adapted to receive compressed air from said primary pressure tank and convert energy in the compressed air into energy for powering said ancillary compressor; and means associated with said primary compressor for selectively taking air from the ancillary pressure tank or the atmosphere and directing said air to the primary compressor.

18. A method for cooling a target in a region having a first pressure comprising the steps of:

(a) providing a compressor for compressing a gas to a second pressure greater than said first pressure;

(b) providing means for cooling the compressed gas to a selected temperature downstream of said compressor; and (c) providing means for discharging said gas towards the target in said region at a selected rate; and (d) providing a pressure tank, downstream of said compressor and upstream of said discharging means, for receiving compressed gas from said compressor and supplying said gas to said discharging means, said cooling means being associated with said pressure tank to cool compressed gas in said pressure tank to the selected temperature;

wherein said second pressure, selected temperature, and selected rate are chosen so as to cool the target upon expansion of the gas in said region.

* * * * *